United States Patent [19]

Hodgkinson

[11] Patent Number: 5,606,093

[45] Date of Patent: Feb. 25, 1997

US005606093A

[54] PROCESS FOR PREPARING N-PHOSPHONOMETHYLGLYCINONITRILE OR DERIVATIVES THEREOF

[75] Inventor: Ian Hodgkinson, Yorkshire, United Kingdom

[73] Assignee: Zeneca Limited, London, United Kingdom

[21] Appl. No.: 532,832

[22] PCT Filed: Mar. 15, 1994

[86] PCT No.: PCT/GB94/00501

§ 371 Date: Oct. 5, 1995

§ 102(e) Date: Oct. 5, 1995

[87] PCT Pub. No.: WO94/22881

PCT Pub. Date: Oct. 13, 1994

[30] Foreign Application Priority Data

Apr. 7, 1993 [GB] United Kingdom ................... 9307234

[51] Int. Cl.$^6$ ................................. C07F 9/38; C07F 9/40
[52] U.S. Cl. ............................... 558/122; 562/17
[58] Field of Search .................. 558/122; 562/17

[56] References Cited

U.S. PATENT DOCUMENTS 3,923,877 12/1975 Barton .
4,083,898 4/1978 Dutra .
4,415,503 11/1983 Robbins .

FOREIGN PATENT DOCUMENTS 68732 1/1983 European Pat. Off. .

*Primary Examiner*—Joseph McKane
*Assistant Examiner*—Michael G. Ambrose
*Attorney, Agent, or Firm*—Joel G. Ackerman

[57] ABSTRACT

A process for the manufacture of an acid salt of an alkyl ester of N-phosphonomethylglycinonitrile is described which comprises reacting methyleneaminoacetonitrile trimer with a trialkylphosphite. The process is carried out under anhydrous conditions and in the presence of an anhydrous acid and an inert solvent in which methyleneaminoacetonitrile trimer is at least partially soluble and the acid salt of the alkyl ester of N-phosphonomethylglycinonitrile product is substantially insoluble. This is followed by recovering the precipitated acid salt of the alkyl ester of N-phosphonomethylglycinonitrile.

10 Claims, No Drawings

PROCESS FOR PREPARING N-PHOSPHONOMETHYLGLYCINONITRILE OR DERIVATIVES THEREOF

This application was filed under 35 USC 371 and is a continuation of PCT International Application No. PCT/GB94/0051, which was filed on Mar. 15, 1994.

The present invention relates to a process for the manufacture of N-phosphonomethylglycinonitrile or salts and esters thereof.

N-phosphonomethylglycinonitrile is a known compound, useful as a herbicide. It may also be converted by hydrolysis into the commercially important herbicide N-phosphonomethylglycine.

N-phosphonomethylglycinonitrile is described for example in U.S. Pat. No. 4,221,583. An alternative process for the manufacture of N-phosphonomethylglycine via the intermediate formation of N-phosphonomethylglycinonitrile is described in U.S. Pat. No. 3,923,877 whilst a related process which is also believed to proceed via N-phosphonomethylglycinonitrile as an intermediate is described in U.S. Pat. No. 4,415,503.

A process for the preparation of a diaryl ester of N-phosphonomethylglycinonitrile is disclosed in U.S. Pat. No. 4,083,898, and in EP-A-0068732 there is disclosed a process for the manufacture of monoesters and diesters of N-alkyl-substituted amino methyl phosphonic acid using a trisubstituted hexahydro-1,3,5-triazine as starting material.

We have now found that the action of a trialkylphosphite phosphonating agent on methyleneaminoacetonitrile trimer in the presence of an acid and an inert solvent provides an improved process which is well adapted to manufacture on a commercial scale and which provides excellent yields of N-phosphonomethylglycinonitrile in the form of a salt of its alkyl ester containing an exceptionally low level of impurities.

According to the present invention there is provided a process for the manufacture of an acid salt of an alkyl ester of N-phosphonomethylglycinonitrile which comprises reacting methyleneaminoacetonitrile trimer with a trialkylphosphite under anhydrous conditions and in the presence of an anhydrous acid and an inert solvent in which the methyleneaminoacetonitrile trimer starting material is at least partially soluble and the acid salt of the alkyl ester of N-phosphonomethylglycinonitrile product is substantially insoluble and thereafter recovering the precipitated acid salt of the alkyl ester of N-phosphonomethylglycinonitrile.

The description methyleneaminoacetonitrile trimer as used herein refers to the compound of formula as shown in Scheme 1 which illustrates the process of the present invention. In Scheme 1, the groups R in the trialkylphosphite (II) represent $C_{1-7}$ alkyl groups and preferably $C_{1-5}$ alkyl groups and the trialkylphosphite is thus preferably a tri ($C_{1-7}$ alkyl)phosphite or a tri($C_{1-5}$ alkyl)phosphite.

The trialkylphosphite is preferably trimethylphosphite, triethylphosphite or tributylphosphite. Trimethylphosphite is a readily available phosphonating agent which is thus a particularly effective feedstock for the commercial manufacture of N-phosphonomethylglycinonitrile. Higher alkyl phosphites such as tributylphosphite and tripentylphosphite may provide advantages in terms of commercial production of product as indicated in more detail below.

Suitable anhydrous acids which can be used in the process of the present invention and which will form an insoluble salt of the alkyl ester of N-phosphonomethylglycinonitrile product will occur to those skilled in the art. Hydrogen halides are especially suitable for use in the process of the present invention. Hydrogen chloride in particular is an effective and readily available anhydrous acid.

The solvent should be inert in the sense that it is not significantly attacked under the reaction conditions, and in particular the solvent should be stable against attack by the trialkylphosphite. Suitable inert solvents in which the methyleneaminoacetonitrile trimer starting material is at least partially soluble and the acid salt of the alkyl ester of N-phosphonomethylglycinonitrile product is substantially insoluble will occur to those skilled in the art. It is to be understood that the methyleneaminoacetonitrile trimer starting material should be at least partially soluble in the inert solvent. By this is meant that the methyleneaminoacetonitrile trimer starting material should be sufficiently soluble that, even though all the starting material may not be dissolved at the commencement of the phosphonation reaction, sufficient will be in solution for the phosphonation reaction to start. Thereafter more starting material will dissolve as the reaction progresses and the starting material in solution is depleted until substantially all the starting material has dissolved by the time the phosphonation reaction is completed. Examples of suitable inert solvents include nitriles such as acetonitrile, esters such as ethyl acetate, haloalkanes such as ethylene dichloride and dichloromethane, ketones such as metylisobutyl ketone, ethers such as diethyl ether or tetrahydrofuran and halogenated aromatic hydrocarbons such as monochlorobenzene. Acetonitrile is an especially effective solvent in which the methyleneaminoacetonitrile trimer is generally completely soluble at the concentrations used in the process of the present invention.

It is not essential that the acid salt of the alkyl ester of N-phosphonomethylglycinonitrile product is completely insoluble in the solvent; it is sufficient that at least a proportion of the acid salt of the alkyl ester of N-phosphonomethylglycinonitrile product precipitates under the reaction conditions and is recovered accordingly. In general, however the acid salt of the alkyl ester of N-phosphonomethylglycinonitrile has a very low solubility in the majority of organic solvents and this represents a particular advantage of the process of the present invention.

The reaction conveniently takes place substantially at ambient temperature although higher or lower temperatures, for example temperatures in the range from −50° C. to 200° C., for example, from −10° C. to 50° C. may be used if desired. Heat may be generated during the course of the reaction and the reaction may if desired be cooled to maintain the temperature substantially at the preferred value, for example, at ambient or slightly above.

When gaseous hydrogen chloride is used as the acid, it may either be passed directly into the reaction mixture or may be added to the reaction mixture as a solution in the dry solvent.

The reaction suitably takes place in the absence of moisture and under non-oxidising conditions, for example under a dry and non-oxidising atmosphere. When gaseous hydrogen chloride is passed directly into the reaction mixture, the gas itself provides the necessary dry and non-oxidising atmosphere. If the hydrogen chloride is added to the reaction mixture as a solution in the dry solvent, it may be desirable to use a suitable inert gas such as dry nitrogen to provide the dry and non-oxidising atmosphere.

Preferably there is used a substantially stoichiometric proportion of trialkylphosphite. The proportion of the acid will depend on the particular acid used. If hydrochloric acid is used, there is preferably employed from 3 to 12 moles of hydrochloric acid per mole of methyleneaminoacetonitrile trimer.

It is a particular advantage of the process of the present invention that the product precipitates in a substantially pure form allowing ready isolation.

Hydrolysis of the alkyl ester of N-phosphonomethylglycinonitrile to N-phosphonomethylglycine or a salt thereof is a well-known process and is described for example in U.S. Pat. No. 3,923,877.

The process of the present invention can be operated as either a batch or continuous or semi-continuous reaction and is particularly well suited to efficient commercial operation and in particular is well suited to integration with a subsequent reaction to form N-phosphonomethylglycine or a salt thereof.

In a typical process, the insoluble acid salt of the alkyl ester of N- phosphonomethylglycinonitrile is recovered from the reaction by filtration whilst the reaction solvent is re-cycled, optionally with a purification stage. The acid salt of the alkyl ester of N-phosphonomethylglycinonitrile is then hydrolysed, for example by treatment with aqueous hydrochloric acid, and N-phosphonomethylglycine is formed.

There are advantages for such a combined process in using a higher trialkylphosphite such as tributylphosphite or tripentylphosphite as phosphonating agent. In particular, the product of the hydrolysis of the butyl or pentyl ester of N-phosphonomethylglycinonitrile is butanol or pentanol respectively. The higher alkanols are immiscible with the aqueous hydrolysis phase and the organic phase can be readily separated and the alkanol re-cycled and used for the formation of more trialkyl phosphite, for example by reaction with phosphorous trichloride. Furthermore, the butyl or pentyl chloride formed in the course of the reaction of the present invention (scheme 1) may conveniently be removed from the reaction solvent (filtrate) by distillation and added to the hydrolysis stage of the butyl or pentyl ester of N-phosphonomethylglycinonitrile where it is itself hydrolysed to form further butanol or pentanol respectively which becomes included in the re-cycle.

Thus according to a further aspect of the present invention there is provided a process for the manufacture of N-phosphonomethylglycine which comprises i) reacting methyleneaminoacetonitrile trimer with tributylphosphite or tripentylphosphite under anhydrous conditions and in the presence of an anhydrous acid and an inert solvent in which the methyleneaminoacetonitrile trimer starting material is at least partially soluble and the acid salt of the alkyl ester of N-phosphonomethylglycinonitrile product is substantially insoluble and thereafter;

ii) filtering the reaction mixture from stage (i) to recover the precipitated acid salt of the alkyl ester of N-phosphonomethylglycinonitrile from the filtrate containing solvent and butyl chloride or pentyl chloride;

iii) hydrolysing the acid salt of the alkyl ester of N-phosphonomethylglycinonitrile under acidic conditions to form N-phosphonomethylglycine and butanol or pentanol;

iv) distilling the filtrate from stage (ii) and re-cycling the solvent to stage (i) and the butyl chloride or pentyl chloride to stage (iii) where it undergoes hydrolysis to form butanol or pentanol respectively;

v) recovering the butanol or pentanol from stage (iii) by phase separation, reacting it with phosphorous trichloride to form tributylphosphite and tripentylphosphite respectively and recycling the tributylphosphite or tripentylphoshite to stage (i); and vi) recovering the N-phosphonomethylglycine product from stage (iii).

The N-phosphonomethylglycine product from stage (iii) is conveniently recovered by crystallisation.

The present invention is illustrated by the following Examples in which all parts and percentages are by weight unless otherwise stated.

EXAMPLE 1

Methyleneaminoacetonitrile trimer 1.7 g (0.0083 g mol) and trimethylphosphite 3.1 g (0.025 g mol) were suspended in 30 ml of ethyl acetate. The mixture was stirred and maintained at about room temperature whilst anhydrous HCl was introduced slowly. During the addition, a white precipitate was formed. GC analysis showed that all the trimer had been consumed after the reaction had been allowed to stand overnight at ambient temperature. The solid was then isolated by filtration and washed with solvent. 3.6 g of product were obtained, corresponding to a 67% yield. The solid was analysed by GC and NMR and was found to be the hydrochloride salt of the dimethyl ester of phosphonomethylglycinonitrile. The product was essentially pure with no significant contaminants identified by GC or NMR.

EXAMPLE 2

The procedure of Example 1 was repeated except that acetonitrile was used as solvent. 3.1 g of essentially pure dimethyl ester of phosphonomethylglycinonitrile was obtained, corresponding to a yield of 56%.

EXAMPLE 3

The procedure of Example 2 was repeated except that 1.825 g (0.05 g mol) of anhydrous HCl was dissolved in 30 ml of acetonitrile prior to addition to the reaction vessel. 3.4 g of essentially pure dimethyl ester of phosphonomethylglycinonitrile was obtained, corresponding to a yield of 63%.

EXAMPLE 4

Methyleneaminoacetonitrile trimer 1.7 g and trimethylphosphite 3.2 g were suspened in 40 ml of dichloromethane. The mixture was stirred and maintained at a temperature below 35° C. whilst anhydrous HCl was introduced over a period of 2 hours. During the addition, a white precipitate was formed. After cooling to 0° C., the product was filtered, washed with 20 ml chilled dichloromethane and dried to give 2.9 g of the dimethyl ester of phophonomethylglycinonitrile (54.1% yield). Proton nmr indicated that the product was essentially pure.

EXAMPLE 5

Methyleneaminoacetonitrile trimer 3.4 g and tributylphosphite (14 g of 90% strength) were dissolved in 40 ml of acetonitrile. The mixture was stirred and maintained at a temperature below 35° C. whilst anhydrous HCl was introduced over a period of 3 hours at a rate of 30 ml/min. During the addition, a white precipitate was formed. After cooling to 0° C., the product was filtered, washed with chilled acetonitrile and dried to give 13.2 g of the dibutyl ester of phophonomethylglycinonitrile (88% yield). Proton nmr indicated that the product was essentially pure.

EXAMPLE 6

The procedure of Example 5 was repeated except that ethyl acetate was used in place of acetonitrile. The methyleneaminoacetonitrile was only partially soluble in the ethyl acetate and was suspended in the reactin mixture. 11.9 g of essentially pure dibutyl ester of phosphonomethylglycinonitrile (79.7% yield) were obtained.

CHEMICAL FORMULAE
(IN DESCRIPTION)
Scheme 1

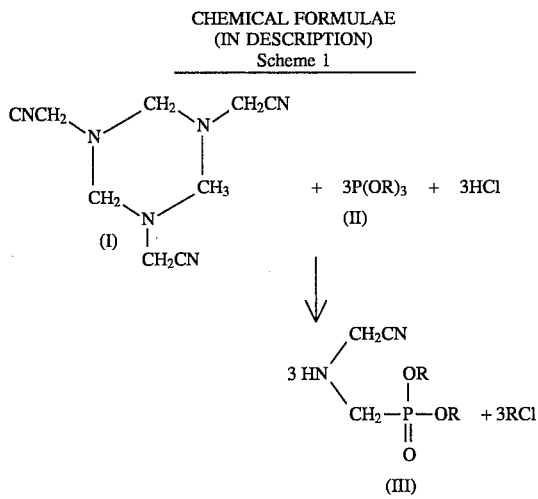

I claim:

1. A process for the manufacture of an acid salt of an alkyl ester of N-phosphonomethylglycinonitrile which comprises reacting methyleneaminoacetonitrile trimer with a trialkylphosphite under anhydrous conditions and in the presence of an anhydrous acid and an inert solvent in which the methyleneaminoacetonitrile trimer starting material is at least partially soluble and the acid salt of the alkyl ester of N-phosphonomethylglycinonitrile product is substantially insoluble and thereafter recovering the precipitated acid salt of the alkyl ester of N-phosphonomethylglycinonitrile.

2. A process according to claim 1 wherein the trialkylphosphite is a tri($C_{1-7}$ alkyl)phosphite.

3. A process according to claim 2 wherein the trialkylphosphite is a tri ($C_{1-5}$ alkyl)phosphite.

4. A process according to any of the preceding claims wherein the anhydrous acid is hydrogen chloride.

5. A process according to claim 4 wherein there is used a substantially stoichiometric proportion of trialkylphosphite and from 3 to 12 moles of hydrochloric acid per mole of methyleneaminoacetonitrile trimer.

6. A process according to claim 1 wherein the inert solvent is a nitrile, an ester, a haloalkane, a ketone, an ether or a halogenated aromatic hydrocarbon.

7. A process according to claim 5 wherein the inert solvent is acetonitrile, ethyl acetate, methyl isobutyl ketone, diethyl ether, tetrahydrofuran, ethylene dichloride, dichloromethane or monochlorobenzene.

8. A process according to claim 1 wherein the reaction takes place at a temperature of from −10° C. to 50° C.

9. A process for the manufacture of N-phosphonomethylglycine which comprises i) reacting methyleneaminoacetonitrile trimer with a trialkylphosphite under anhydrous conditions and in the presence of an anhydrous acid and an inert solvent in which the methyleneaminoacetonitrile trimer starting material is at least partially soluble and the acid salt of the alkyl ester of N-phosphonomethylglycinonitrile product is substantially insoluble and thereafter ii) recovering the precipitated acid salt of the alkyl ester of N-phosphonomethylglycinonitrile and iii) hydrolysing the acid salt of the alkyl ester of N-phosphonomethylglycinonitrile to form N-phosphonomethylglycine.

10. A process for the manufacture of N-phosphonomethylglycine which comprises i) reacting methyleneaminoacetonitrile trimer with tributylphosphite or tripentylphosphite under anhydrous conditions and in the presence of an anhydrous acid and an inert solvent in which the methyleneaminoacetonitrile trimer starting material is at least partially soluble and the acid salt of the alkyl ester of N-phosphonomethylglycinonitrile product is substantially insoluble and thereafter;

ii) filtering the reaction mixture from stage (i) to recover the precipitated acid salt of the alkyl ester of N-phosphonomethylglycinonitrile from the filtrate containing solvent and butyl chloride or pentyl chloride;

iii) hydrolysing the acid salt of the alkyl ester of N-phosphonomethylglycinonitrile under acidic conditions to form N-phosphonomethylglycine and butanol or pentanol;

iv) distilling the filtrate from stage (ii) and re-cycling the solvent to stage (i) and the butyl chloride or pentyl chloride to stage (iii) where it undergoes hydrolysis to form butanol or pentanol respectively;

v) recovering the butanol or pentanol from stage (iii) by phase separation, reacting it with phosphorous trichloride to form tributylphosphite and tripentylphosphite respectively and recycling cycling the tributylphosphite or tripentylphoshite to stage (i); and vi) recovering the N-phosphonomethylglycine product from stage (iii).

* * * * *